US007176327B2

(12) United States Patent
Sadler et al.

(10) Patent No.: US 7,176,327 B2
(45) Date of Patent: Feb. 13, 2007

(54) PHOTOREACTIVE COMPOUNDS AND COMPOSITIONS

(75) Inventors: Peter John Sadler, Penicuik (GB); Philippe Muller, Hitchin Herts (GB)

(73) Assignee: University Court of the University of Edinburgh, Edinburgh (GB)

( * ) Notice: Subject to any disclaimer, the term of this patent is extended or adjusted under 35 U.S.C. 154(b) by 352 days.

(21) Appl. No.: 10/487,758

(22) PCT Filed: Aug. 27, 2002

(86) PCT No.: PCT/GB02/03939

§ 371 (c)(1),
(2), (4) Date: Feb. 24, 2004

(87) PCT Pub. No.: WO03/017993

PCT Pub. Date: Mar. 6, 2003

(65) Prior Publication Data

US 2004/0248873 A1 Dec. 9, 2004

(30) Foreign Application Priority Data

Aug. 27, 2002 (GB) .................. 0120618.4

(51) Int. Cl.
C07F 15/00 (2006.01)
A61K 31/28 (2006.01)
(52) U.S. Cl. ..................... 556/137; 514/492
(58) Field of Classification Search ........ 556/137; 514/492

See application file for complete search history.

(56) References Cited

U.S. PATENT DOCUMENTS

| 4,119,653 A | 10/1978 | Tobe et al. | 260/429 |
| 4,119,654 A | 10/1978 | Tobe et al. | 260/429 |
| 4,250,189 A | 2/1981 | Hydes et al. | 424/287 |

FOREIGN PATENT DOCUMENTS

CH        632 672 A5    10/1982

OTHER PUBLICATIONS

Vorob'EV-Desyatovskii et al., Zhurnal Obshchei Khimii, vol. 60, No. 2, pp. 258-266 (1990).*
J. Biol. Inorg. Chem., vol. 8, pp. 741-745 (2003).*
Chemical Abstracts Service, Columbus, OH, Vorob'ev-Desyatovskii N.V. et al., "Pyridine migration induced by oxidation of azide ion in (azido)(pyridine)platinum complexes", Zhurnal Obshchei Khimii (1990), 60(2), pp. 258-266.

* cited by examiner

*Primary Examiner*—Porfirio Nazario-Gonzalez
(74) *Attorney, Agent, or Firm*—Gifford, Krass, Groh, Sprinkle, Anderson & Citkowski, P.C.

(57) ABSTRACT

The present invention provides a compound of formula (I): $Pt^{IV}(N_3)_2 X^1 X^2 Y^1 Y^2$, wherein $X^1$ and $X^2$ are the same or different and each one is a group $NR^1R^2R^3$ wherein $R^1$, $R^2$ and $R^3$ are the same or different and each can be any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group $R^1R^2NR^4NR^1R^2$ wherein $R^1$ and $R^2$ have the same meaning as before, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or when cis together represent a divalent moiety $Y^3$, wherein at least one of $Y^1$ and $Y^2$, or $Y^3$, is a substantially labile ligand in the analogous Pt(II) complex without the azide groups, while being substantially resistant, in vivo, to hydrolysis and physiological reducing agents. One or more of $R^1$, $R^2$, $R^3$ and $R^4$, may further represent a covalently bonded link to at least one further complex of formula (I) to form a dimer or oligomer, or to a targeting moiety having affinity for a predetermined tissue or cell type.

17 Claims, No Drawings

PHOTOREACTIVE COMPOUNDS AND COMPOSITIONS

FIELD OF THE INVENTION

The present invention relates to novel photoreactive compounds and compositions, their preparation and their use in the preparation of chemotherapeutic agents as anticancer drugs.

BACKGROUND OF THE INVENTION

Cisplatin (cis-[PtCl$_2$(NH$_3$)$_2$]) is one of the most widely used platinum (Pt) based therapeutic anticancer drugs. Such Pt(II) compounds do, however, exhibit severe side effects due to their indiscriminate and uncontrollable cytotoxic effects which include nausea, neurotoxicity and renal toxicity. The drug is believed to exert its cytotoxicity through binding DNA, particularly to adjacent GG bases. Additional disadvantages of Pt(II) based drugs are associated with their intravenous administration route, which requires increased medical attention and often results in additional complications and discomfort for the patient than would be the case if oral administration was possible. Another problem frequently associated with the use of cisplatin is the acquired resistance of tumour cells to the drug following an initial treatment.

Such disadvantages have prompted the search for alternative and improved anticancer drugs and therapies. Presently clinical trials are underway using oral administration of Pt(IV) compounds such as the Johnson-Matthey compound JM216. Pt(IV) compounds are substantially inert to substitution and can act as a good precursor for highly reactive Pt(II) compounds, which readily undergo substitution. Ideally, such conversion of Pt(IV) to Pt(II) would occur at the target side of the tumour in a controlled manner. The presently available Pt(IV) compounds are, however, thought to be reduced to active Pt(II) species in the blood and, hence, are also accompanied by the adverse side effects of indiscriminate cytotoxicity associated with cisplatin. Blood plasma is particularly rich in powerful reducing agents such as glulathione (GSH), cysteine, and ascorbate, whereby, once administered to the body, Pt(IV) compounds are vulnerable to reduction and activation.

Another anti-cancer strategy which has been used, namely photodynamic therapy, entails irradiation with visible or near-infrared light to generate, highly reactive and cytotoxic, singlet oxygen species via porphyrin mediated conversion of triplet oxygen. Advances in lasers and fibre optics has enabled more or less highly localised delivery of the light to tumours of epithelial origin. Such targeted cytotoxicity is highly desirable in the treatment of tumours and there is a need for a compound which is substantially stable both ex vivo, and in vivo after administration, but is activatable to a cytotoxic form in a spatially and temporally controlled manner whilst being substantially non-toxic and physiologically acceptable prior to activation, and it is an object of the present invention to provide such a compound.

SUMMARY OF THE INVENTION

The present invention overcomes many of the disadvantages of existing Pt-based anti-cancer drugs by providing novel, water soluble, biologically inert Pt(IV) compounds which can be converted to a cytotoxic Pt(II) species by photoactivation.

DETAILED DESCRIPTION OF THE PREFERRED EMBODIMENTS

In a first aspect, the present invention provides novel compounds which are Pt(IV) complexes of the general formula I:

$$Pt(N_3)_2X^1X^2Y^1Y^2 \quad \text{(I)}$$

wherein $X^1$ and $X^2$ are the same or different and each one represents a group of the general formula NR$^1$R$^2$R$^3$ wherein R$^1$, R$^2$ and R$^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula R$^1$R$^2$NR$^4$NR$^1$R$^2$ wherein R$^1$ and R$^2$ have the same meaning as hereinbefore, and R$^4$ represents an optionally substituted divalent, saturated or unsaturated, alkyl chain preferably having 2 or 3 carbon atoms between the N atoms, an optionally substituted divalent, saturated or unsaturated cycloalkyl or an optionally substituted divalent aryl, or R$^4$ or two or more of R$^1$, R$^2$, R$^3$ and R$^4$ and the respective N atom(s) to which they are linked, represent an optionally substituted heterocyclyl having at least one ring containing said N atom(s); and Y$^1$ and Y$^2$ are the same or different or, when in a cis position, as a further alternative they may together represent a divalent moiety Y$^3$, wherein at least one of Y$^1$ and Y$^2$, or Y$^3$, is a substantially labile ligand in the analogous Pt(II) complex corresponding to general formula (I) without the azide groups, whilst being substantially resistant, in vivo, to hydrolysis and physiological reducing agents, and one or more of R$^1$, R$^2$, R$^3$ and R$^4$, may represent a covalently bonded link to at least one further complex of formula I so as to form a dimer or oligomer, or to a targeting moiety having affinity for a predetermined tissue or cell type; and wherein $X^1$ and $X^2$ are preferably in a cis configuration.

Where any of the groups in general formula I have been indicated as being optionally substituted then each of the substituents could be selected from hydroxyl, alkoxyl, aralkoxyl, carboxy, halogen, trihaloalkyl, and carbonyl.

Where two or more of R$^1$, R$^2$, R$^3$ and R$^4$ and the respective N atom represent heterocyclyl, typical examples of NR$^1$R$^2$R$^3$ include pyridyl, quinolyl, isoquinolyl and picolyl, whilst typical examples of R$^1$R$^2$NR$^4$NR$^1$R$^2$ include bipyridyl, phenanthrolyl, 1,2-diaminophenyl and 1,2-diaminocyclohexyl.

For the avoidance of doubt, unless otherwise indicated to the contrary, the following terms have the indicated meanings:

"Alkyl" includes unsubstituted and substituted, straight and branched, chain groups, which are generally C1 to C10, preferably C1 to C6 (i.e. have 1 to 10, preferably 1 to 6 carbon atoms in the alkyl chain).

"Cycloalkyl" includes unsubstituted and substituted cycloalkyl groups, which are generally C3 to C8, preferably C3 to C6.

"Alkenyl" includes unsubstituted and substituted, straight and branched, chain groups, which are generally C1 to C10, preferably C1 to C6, and have at least one double bond in the chain.

"Cycloalkenyl" includes unsubstituted and substituted cycloalkyl groups which are generally C4 to C8, preferably C4 to C6, and have at least one double bond in the ring.

"Alkynyl" includes unsubstituted and substituted, straight and branched, chain groups, which are generally C1 to C10, preferably C1 to C6, and have at least one triple bond in the chain.

"Aryl" includes unsubstituted and substituted aromatic groups having at least one aromatic ring, usually a C6 ring.

"Heterocyclyl" includes unsubstituted and substituted cyclic groups having at least one ring which generally has from 3 to 7 atoms in the ring, of which at least one is a heteroatom selected from N, O and S. Typical examples having at least one N atom include pyridine, pyrrole, pyrimidine, pyridazine, pyrazole and imidazole. Typical examples having at least one O atom include furan and glucose. A typical example having at least one S atom is thiophene. Typical examples having at least two different hetero atoms include oxazole and thiazole.

"Aralkyl" includes alkyl groups as defined hereinbefore which have an aryl substituent, for example, benzyl or phenethyl, and may be unsubstituted or substituted.

"Alkoxyl" (or alkoxy) has the same meaning as alkyl when bonded to oxygen, for example, methoxy.

"Aryloxyl" (or aryloxy) and "Aralkyl" (or alkaryloxy) have the same meaning as aryl and aralkyl when bonded to oxygen, for example phenoxy or benzyloxy.

It will be appreciated that in order to reduce the dosage required of the compounds of the present invention, these may, as indicated above, incorporate a targeting moiety having affinity for a predetermined tissue or cell type. Suitable moieties include, for example, aminophosphonate ligands which tend to bind to bone and thus have particular utility in the use of compounds of formula I for the treatment of bone cancers, or a receptor-specific ligand such as, for example, serotonin. It is also possible to utilise Pt(IV) complexes of the present invention which are bound to suitable polymeric or dendrimeric materials in generally known manner, in order to facilitate delivery thereof to a desired site in the body.

As noted herein before two or more complexes of general formula I may be linked together so as to form a dimer or oligomer. Various kinds of link may be used. One convenient form of link in the case of an $R^1$ and/or $R^2$ group is an alkyl chain, generally an at least C4, preferably a C4 to C8 chain.

Suitably labile $Y^1$ and $Y^2$ ligands generally comprise halogen, especially chlorine, or more preferably, an $OY^4$ group wherein $Y^4$ represents H or a $Y^5CO$ group wherein $Y^5$ represents R, RNH, or RCS, wherein R represents an optionally substituted C1 to C12 alkyl. Suitably labile $Y^3$ ligands include groups of the general formula $OOC(CY^6Y^7)_n CY^8Y^9O$ wherein each of $Y^6$ and $Y^7$ can represent H or a substituent or $Y^6$ and $Y^7$ together represent cycloalkyl, and n is 0, 1 or 2 and each of $Y^8$ and $Y^9$ can represent H or a substituent, or together represent oxygen.

Preferred examples of $Y^3$ include oxalate and 1,1-dicarboxycyclobutane (CBDCA).

Advantageously one or more of the $R^1$, $R^2$, $R^3$, $R^4$, $Y^1$, $Y^2$ and $Y^3$ groups is chosen so as to promote solubility in polar solvents, especially water or to enhance lipophilicity, in order to facilitate delivery of the complexes of formula I to a desired site in the body. Lipophilicity may be enhanced by the presence of aromatic groups or hydrocarbon chains having an extended chain length. Water solubility may be enhanced by the presence of polar groups such as carboxylate groups (for example those present in any of the $Y^1$, $Y^2$ and $Y^3$ groups), and/or salt forming groups. In the latter case salts are desirably formed with physiologically acceptable counterions.

Particularly preferred compounds of formula I which may be mentioned include:

Cis,trans,cis-[$Pt^{IV}(N_3)_2(OH)_2(NH_3)_2$];

Cis,trans-[$Pt^{IV}(en)(N_3)_2(OH)_2$] (where en represents ethylenediamine);

Trans, cis, cis-[$Pt^{IV}(OCOCH_3)_2(N_3)_2(NH_3)_2$];

[$Pt^{IV}(NH_3)_2(CBDCA)trans-(N_3)_2$] (where CBDCA represents 1,1-dicarboxycyclobutane);

Cis,trans-[cis-dach($N_3)_2(OH)_2$] (where dach represents diaminocyclohexane)

In a modified form of the invention only one of $Y^1$ and $Y^2$ is a labile ligand and the other could represent any other convenient group which is resistant to hydrolysis and physiological reducing agents or could represent a further $N_3$ group or a $X^3$ group wherein $X^3$ may be the same as or different to $X^1$ and $X^2$ and has the same general formula as $X^1$ and $X^2$.

Compounds of formula I have been found to have good stability in aqueous solution, as well as in blood plasma, saline solution and glutathione (GSH) aqueous solution, with individual compounds having been found to be stable in aqueous solution for 2 months or more (when kept in the dark) with little or no azide ligands being replaced or substituted. A particular advantage of the present invention is the substantial stability of the compounds of formula I in blood plasma. Previously known orally active-Pt(IV) based drugs are reduced to Pt(II) in blood plasma. Compounds of the present invention have been found to remain inert and stable under physiological conditions, including blood plasma and GSH solution, overcoming existing problems associated with oral administration of less stable Pt(IV) compounds. Resistance to reduction by glutathione (GSH) is particularly advantageous as this "physiological" reducing agent is particularly powerful and prevalent under normal physiological conditions.

The relative inertness of the compounds of the present invention may, though, be readily overcome by photoactivation, with the Pt(IV) azide compounds of the present invention being converted to active Pt(II) compounds which may include compounds of formula II:

$$PtX^1X^2Y^1Y^2 \qquad (II)$$

upon photoactivation.

Photoactivation may be effected by use of radiation of suitable wavelength. In general there may be used radiation having a wavelength of from 350 to 800 nm, preferably from 450 to 500 nm, most preferably about 458 nm which has been found to be particularly efficient at photoactivating the compounds of the present invention. Radiation of longer wavelength within the preferred range can be used, for example, red light which has better penetration through body tissue, though lower energy and photoactivation of the compounds of the present invention has been achieved using red light of, for example, 647 nm wavelength. It is possible to increase the effectiveness of the longer wavelength radiation, such as red light, by employing techniques such as frequency doubling lasers so as to deliver to the target site radiation with the desired increased energy levels over that of longer wavelength red light, for photo reduction of the Pt(IV) complexes to Pt(II) complexes.

By controlling and targeting the photoactivating radiation, the conversion of the relatively inert Pt(IV) compounds of formula I into active Pt (II) compounds may be effected in a more or less precisely spatially and temporally controlled manner.

The compounds of the present invention and their products following photoactivation have been analysed by a number of techniques including 1D $^1$H and 2D [$^1$H, $^{15}$N] heteronuclear-single-quantum coherence (HSQC) NMR spectroscopy, 2D [$^1$H, $^{15}$N] HSQC-total correlation spectroscopy (HSQC-TOCSY) NMR spectrometry, electrospray mass spectrometry, and X-ray crystallography, which has confirmed their structure and identified their reaction products under various conditions. These techniques have also been used to show that following photoactivation of the Pt(IV) complexes to Pt(II) complexes, the photoactivated products bind to GMP (guanosine monophosphate), GG dinucleotide and polynucleotides showing them to be suitable for use as cytotoxic agents for use in cancer therapy, whose cytotoxicity may be targeted and controlled.

With regard to products obtained following irradiation of the compounds of formula I, NMR spectroscopy data which has been obtained indicates that in at least some cases, a number of different more or less stable Pt(II) complex species is obtained from a given Pt(IV) compound of formula I. In a further aspect the present invention provides as new products and/or intermediate reactive species, especially for use in cancer therapy, any such compounds or intermediate reactive species which are novel.

The skilled addressee will appreciate that compounds of formula I may be obtained in different cis- and trans-form configurations of the azide, $X^1$ and $X^2$, and $Y^1$ and $Y^2$ groups, and it should be understood that all of these are encompassed within the scope of the present invention. Where one of $Y^1$ and $Y^2$ is also an azide or $X^1/X^2$ group, so that there are three identical groups, it will be appreciated that these could be present in different isomeric forms viz mer, where the three identical groups are all cis to each other, or fac, where the three groups are coplanar.

The compounds of the present invention can be prepared by any suitable method known in the art for compounds of similar structure. For example a compound of the formula $Pt^{II}(N_3)_2X^1X^2$ may be oxidized to a compound of the formula $Pt^{IV}(N_3)_2X^1X^2Q^1Q^2$ wherein $Q^1$ and $Q^2$ may be the same as $Y^1$ and $Y^2$ as defined hereinbefore or different, and where $Q^1$ and/or $Q^2$ is a group(s) other than $Y^1$ or $Y^2$, respectively, or together represent a group other than $Y^3$, replacing any such $Q^1$, $Q^2$ or $Q^3$ group with said $Y^1$, $Y^2$ or $Y^3$ group(s). In general compounds of general formula I wherein $Y^1$ and $Y^2$ are both OH can be readily made by oxidation of the analogous PtII compound in which $Y^1$ and $Y^2$ are absent, with hydrogen peroxide so as to add the OH groups. Other compounds of general formula I can then be made by reacting the abovementioned OH-group containing compound with a suitable reactant so as to replace or condense with the OH group. Thus, for example, reaction with a carboxyalkyl anhydride would yield the corresponding carboxyalkyl substituted compound of general formula I. Further details of suitable processes are described in the literature, for example, in "Platinum and other Metal Coordination Compounds in Cancer Chemotherapy", Plenum Press, New York (1991) at pp. 93–100.

The analogous PtII compounds referred to above are conveniently obtainable by reaction of a compound of general formula III:

$PtX^1X^2Z^1Z^2$ (III)

wherein $X^1$ and $X^2$ have the same meaning as before and $Z^1$ and $Z^2$ are conveniently halogen, for example, I or Cl, with silver nitrate to facilitate replacement of the halogen moiety with an azide moiety, in generally known manner.

Another route for obtaining compounds of general formula I is by means of a substitution reaction with the analogous Pt(IV) compound of formula IV:

$PtX^1X^2Y^1Y^2Z^3Z^4$ (IV)

wherein $X^1$, $X^2$, $Y^1$ and $Y^2$ have the same meaning as in formula I, and $Z^3$ and $Z^4$ are the same or different and each is a suitably labile leaving group such as hydroxyl. The compound of formula IV may be reacted with excess azide salt, conveniently sodium azide.

The compounds of the present invention can be used to treat various kinds of tumours including non-malignant tumours and malignant tumours including breast, ovarian, skin, mouth, throat, colon, gastro-intestinal tract, and colorectal carcinomas, as well as leukaemias, myelomas, lymphomas and other such disorders of the blood and lymphatic system.

Thus in a further aspect the present invention provides a method of treating a cancer in a patient comprising the steps of administering a compound which is a complex of formula I to the patient, and subsequently irradiating said compound with light. In the case of a tumour of a body tissue, the tumour itself will normally be irradiated in situ. In the case of conditions such as leukaemias and other such circulatory disorders, there would generally be used a suitable targeting moiety, for example a suitable antibody for binding the complex to the abnormal cells. In such cases it would generally be convenient to carry out the irradiation step extra-corporeally, by passing blood from the patient through an irradiation apparatus, and then returning the treated blood to the patient.

In another aspect the present invention provides a method of treatment of a tumour in a patient comprising the steps of administering a compound which is a complex of formula I to the patient, and subsequently irradiating the tumour with light. It will be appreciated that the light radiation intensity and dose should be sufficient to penetrate the tumour and convert an effective amount, preferably substantially all, of the amount of the compound of formula I present in and/or on the tumour.

The present invention can in principle be used to treat any condition in which it is desired, selectively to kill off abnormal or cells present in the body. Where the cells are not localized, then it would normally be necessary to use a suitable targeting moiety to localize the compounds of the invention in direct proximity to said cells upon administration thereof.

Thus in yet another aspect the present invention provides a method of treatment of a condition in a patient in which abnormal cells are present in the body, comprising the steps of:

providing a compound comprising a complex of formula I as defined hereinbefore wherein one or more of $R^1$, $R^2$, $R^3$ and $R^4$ represents a covalently bonded link to a targeting moiety having affinity for said abnormal cell;

administering said compound to the patient; and irradiating the compound.

As discussed above the compound may be irradiated directly in the body or extra-corporeally.

In another aspect the present invention provides a pharmaceutical formulation comprising a compound of formula I as defined hereinbefore, or a pharmaceutically acceptable salt thereof, together with a pharmaceutically acceptable carrier therefor.

Formulations according to the present invention include those suitable for systemic administration as well as those suitable for direct application to the tumour. More particularly they include oral, topical, rectal or parenteral (including intravenous) administration. Preferred formulations are those suitable for oral, or parenteral administration.

The formulations may conveniently be presented in unit dosage form and may be prepared by any of the methods well known in the art of pharmacy. All methods include step of bringing the active compound into association with a carrier which constitutes one or more accessory ingredient. In general, the formulations are prepared by uniformly and intimately bringing the compound of the present invention into association with a liquid carrier or a finely divided solid carrier or both and then, if necessary, shaping the product into desired formulations.

Formulations of the present invention suitable for oral administration may be presented as discrete units as capsules, cachets, tablets or lozenges, each containing a predetermined amount of the active compound; as a powder or granules; or a solution or suspension in an aqueous or non-aqueous liquid such as a syrup, an elixir, an emulsion or a draught. Other kinds of formulations such as teas or infusions, may also be used.

A tablet may be made by compression or moulding, optionally with one or more accessory ingredient(s). Compressed tablets may be prepared by compressing in a suitable machine the active compound in a free-flowing form, such as a powder or granules, optionally mixed with a binder, lubricant, inert diluent, surface active or dispersing agent. Moulded tablets may be made by moulding in a suitable matching a mixture of the powdered active compound with any suitable carrier.

A syrup may be made adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter. Formulations suitable for parenteral administration conveniently comprise a sterile aqueous preparation of the active compound which is preferably isotonic with the blood of the recipient. Such formulations suitably comprise a solution of a compound of Formula (I) that is isotonic with the blood of the recipient.

Useful formulations also comprise concentrated solutions or solids containing a compound of the present invention which upon dilution with an appropriate solvent give a solution for parenteral administration as above.

In addition to the aforementioned ingredients, formulations of this invention may further include one or more accessory ingredient(s) selected from diluents, buffers, flavouring agents, binders, surfactants, thickeners, lubricants, preservatives (including antioxidants) and the like.

Further preferred features and advantages of the invention will appear from the following examples provided for the purposes of illustration.

Experimental Procedures

In Examples 1 and 2, $^{15}N$ (greater than 98% abundance of the $^{15}N$ isotope) $NH_4Cl$ (obtained from Aldrich of Gillingham, UK) and ethylenediamine (en) (prepared by ourselves from $N^{15}$ phthalimide using the method described in E. Zang & P. J. Sadler in Synthesis 1997 pp 410–412), were used in order to facilitate the use of NMR spectroscopy for the purposes of investigating the properties of the novel compounds obtained. It will of course be understood that normally there would be used natural abundance $^{15}N$ materials, and the preparative procedures using the latter materials would be substantially identical to those described in Examples 1 and 2. Example 3 describes such an equivalent procedure for Example 1, and Example 4 describes an alternative procedure for Example 2 using natural abundance $^{15}N$ materials, though enriched $^{15}N$ materials could likewise be used.

NMR spectroscopy was carried out using procedures as described in detail in S. J. Berners-Price & P. J. Sadler, Coordination Chemistry Reviews 151 (1996) at pp 19–26, by 1D $^1H$ and 2D [$^1H$, $^{15}N$] heteronuclear-single-quantum coherence (HSQC) NMR spectroscopy and in the case of cis,trans-[$Pt^{IV}(en)(N_3)_2(OH)_2$] also 2D [$^1H$, $^{15}N$] HSQC-total correlation spectroscopy (HSQC-TOCSY) NMR spectroscopy.

EXAMPLE 1

Preparation of Cis,trans,cis-[$Pt^{IV}(N_3)_2(OH)_2(NH_3)_2$]

$K_2[PtCl_4]$ (1 g, 2.41 mmol) was dissolved in 50 ml deionized water in a 100 ml round-bottomed flask. 10 molar equivalents (mol eq.) of KI was added and the solution stirred for 30 min. at room temperature. 2 mol eq. of $^{15}NH_4Cl$ (0.26 g, 4.88 mmol) was added to the solution. The pH was adjusted with 1 M NaOH to 11. The yellow precipitate was filtered and washed with water, ethanol and ether. The yellow solid (cis-[$Pt(^{15}NH_3)_2I_2$]) was dried in a desiccator over silica gel. cis-[$Pt(^{15}NH_3)_2I_2$] (0.2 g, 0.43 mmol) and 2 mol eq. $AgNO_3$ (0.146 g, 0.86 mmol) was added in a round-bottomed flask. 20 ml deionized water was added and the suspension was stirred in the dark for 24 hours. The AgI-precipitate was twice filtered off with an inorganic membrane filter (Whatman, Anotop 10, 0.02 μm). 20 mol eq. of $NaN_3$ (0.57 g, 8.77 mmol) was added and the solution stirred for 30 min. in the dark at room temperature. The solvent volume was reduced to 10 ml and the flask put in the fridge overnight. The yellow precipitate was washed with ether and dried in air. Yield: 97 mg (72%). 10 ml of deionized water was added to cis-[$Pt(N_3)_2(NH_3)_2$] (0.086 g, 0.27 mmol). 40 eq. of $H_2O_2$ (1.2 ml 30% $H_2O_2$, 11.75 mmol) was added and the solution stirred in the dark at room temperature for 24 hours. The volume of the solution was reduced and the flask put in the fridge (4° C.) for 2 days. The yellow precipitate of cis,trans,cis-[$Pt^{IV}(N_3)_2(OH)_2(NH_3)_2$] was filtered and washed with water and ether.

Yield: 32.8 mg (35%)

EXAMPLE 2

Preparation of Cis,trans-[$Pt^{IV}(en)(N_3)_2(OH)_2$]

$^{15}N$-en.2HCl (0.052 g, 0.39 mmol) was dissolved in 10 ml deionized water and the pH adjusted to 8 with 1 M NaOH. $K_2[PtCl_4]$ (0.162 g, 0.39 mmol) was added and the solution stirred at room temperature. The pH was regularly adjusted to 8–9. The obtained yellow precipitate ([$Pt(^{15}N$-en)$Cl_2$])

was washed with water and ether and dried over $P_2O_5$. [Pt($^{15}$N-en)Cl$_2$] (0.04 g, 0.12 mmol) and 2 mol eq. AgNO$_3$ (0.041 g, 0.24 mmol) were stirred in deionized water in the dark at room temperature for 24 hours in a round-bottomed flask. The white precipitate (AgCl) was twice filtered off with an inorganic membrane filter (Whatman, Anotop 10, 0.02 μm). 25 mol eq. NaN$_3$ (0.208 g, 3.2 mmol) was added to the solution. The volume of the solution was reduced and the flask put in the fridge for 2 days. The yellow precipitate was filtered and washed with water and ether. Yield: 23.5 mg (57%)

5 ml deionized water was added to [Pt(en)(N$_3$)$_2$] (0.021 g, 0.06 mmol) in a 25 ml round-bottomed flask. 50 mol eq. of $H_2O_2$ (0.3 ml 30% $H_2O_2$, 2.9 mmol) was added to the solution which was then stirred in the dark at room temperature for 24 hours. The yellow precipitate of cis,trans-[Pt$^{IV}$(en)(N$_3$)$_2$(OH)$_2$] was filtered and washed with water and ether. Yield: 10 mg (40%).

EXAMPLE 3

Preparation of Cis,trans,cis-Pt$^{IV}$(N$_3$)$_2$(OH)$_2$(NH$_3$)$_2$]

KI (5.61 g, 33.79 mmol) was added to an aqueous solution of K$_2$[PtCl$_4$] (1.40 g, 3.38 mmol, 50 ml). After stirring for 30 min at ambient temperature, NH$_4$Cl (0.362 g, 6.76 mmol) was added and the pH adjusted to 11 with 1 M NaOH. A yellow precipitate (cis-[Pt(NH$_3$)$_2$I$_2$]) appeared which was filtered off and washed with water, ethanol and ether and dried under vacuum to yield 1.41 g (87%). AgNO$_3$ (2 mol equiv, 0.32 g, 1.89 mmol) was added to a suspension of cis-[Pt(NH$_3$)$_2$I$_2$] (0.455 g, 0.94 mmol) in water (20 ml) which was then stirred in the dark for 24 h. The AgI-precipitate was filtered off with an inorganic membrane filter (Whatman, Anotop 10, 0.02 μm). NaN$_3$ (20 mol equiv, 1.23 g, 18.86 mmol) was added and the solution stirred for 30 min in the dark at ambient temperature. The solvent volume was reduced to 10 ml and the flask was stored at 4° C. overnight. A yellow precipitate of cis-[Pt(N$_3$)$_2$(NH$_3$)$_2$] was obtained and washed with ether and dried in air to yield 212 mg (72%).

$H_2O_2$ (40 mol eq., 1.2 ml 30% $H_2O_2$, 11.75 mmol) was added to a suspension of cis-[Pt(N$_3$)$_2$(NH$_3$)$_2$] (0.086 g, 0.27 mmol) in water (10 ml) which was stirred in the dark at ambient temperature for 24 h. The volume of the solution was reduced and on cooling to 4° C., cis,trans,cis-[Pt$^{IV}$(N$_3$)$_2$(OH)$_2$(NH$_3$)$_2$] formed as a yellow precipitate which was filtered and washed with water and ether to yield 32.8 mg (35%). Crystals suitable for x-ray crystal structure determination were grown from a water/ethanol (1/1 v/v) mixture at 4° C.

EXAMPLE 4

Preparation of Cis,trans-[Pt$^{IV}$(en)(N$_3$)$_2$(OH)$_2$]

K$_2$[PtCl$_4$] (1.48 g, 3.57 mmol) was added to an aqueous solution of KI (30 ml, 5.51 g, 33.19 mmol) and the solution stirred at ambient temperature. Ethylenediamine (238 μl, 3.57 mmol) was added to the dark brown solution. The yellow precipitate ([Pt$^{II}$(en)I$_2$]) was washed with water and ether and dried under vacuum to yield 1.67 g (92%). [Pt$^{II}$(en)I$_2$] (0.68 g, 1.34 mmol) and 2 mol eq. AgNO$_3$ (0.453 g, 2.67 mmol) were stirred in water in the dark at room temperature for 24 hours. The AgI precipitate was filtered off and 25 mol eq. NaN$_3$ (1.74 g, 26.72 mmol) was added to the solution. The volume was reduced and a yellow precipitate was obtained on cooling of the solution to 277 K. This was washed with water and ether to yield 0.247 mg (55%) of [Pt$^{II}$(en)(N$_3$)$_2$]. $H_2O_2$ (25 mol eq., 1.5 ml 30% $H_2O_2$, 14.5 mmol) was added to a suspension of [Pt(en)$^{II}$(N$_3$)$_2$] (0.187 g, 0.55 mmol) in water (15 ml). This was then stirred in the dark at ambient temperature for 24 h. The yellow precipitate of cis,trans-[Pt$^{IV}$(en)(N$_3$)$_2$(OH)$_2$] was filtered and washed with water and ether to yield 79 mg (38%). Crystals suitable for x-ray crystal structure determination were obtained from an aqueous solution at 4° C.

EXAMPLE 5

Preparation of Trans,cis,cis-Pt$^{IV}$(OCOCH$_3$)$_2$(N$_3$)$_2$(NH$_3$)$_2$]

Deionized water (5 ml) was added to cis-[Pt$^{II}$(N$_3$)$_2$(NH$_3$)$_2$] (0.028 g, 0.09 mmol). $H_2O_2$ (0.5 ml 30% $H_2O_2$, 4.9 mmol) was added and the solution stirred overnight at room temperature in the dark. The solvent was then removed on a rotary evaporator and the yellow precipitate dried overnight under vacuum. 5 ml dichloromethane was added to the yellow precipitate. 4 ml of acetic anhydride (42.4 mmol) was dropwise added under cooling with an ice bath. The suspension was stirred for one week in the dark. The pale yellow precipitate of trans,cis,cis-[Pt$^{IV}$(OCOCH$_3$)$_2$(N$_3$)$_2$(NH$_3$)$_2$] was filtered with a paper filter and washed with cold water and ether and then dried over silica gel. Yield: 25 mg (64%). Crystals suitable for x-ray crystal structure determination were obtained from an aqueous solution at 4° C.

EXAMPLE 6

Preparation of Cis,trans-[Pt$^{IV}$(cis-dach)(N$_3$)$_2$(OH)$_2$] (dach=diaminocyclohexane)

cis-Diaminocyclohexane (120 μl, 1 mmol) was added to an aqueous solution of K$_2$[PtCl$_4$] (0.45 g, 1.08 mmol, 30 ml) and stirred for 30 min at ambient temperature. The yellow precipitate ([Pt$^{II}$(cis-dach)Cl$_2$)]) was filtered and washed with water and ether to yield 165.6 mg (40%). AgNO$_3$ (0.144 g, 0.85 mmol) was added to a suspension in water of [Pt$^{II}$(cis-dach)Cl$_2$)] (0.165 g, 0.44 mmol, 20 ml) and stirred overnight at 333 K in the dark. The white AgCl precipitate was filtered off with an inorganic membrane filter (Whatman, Anotop 10, 0.02 μm). NaN$_3$ (0.56 g, 8.61 mmol) was added which led to a colour change to yellow. The solution was stirred for 2 h at ambient temperature in the dark before filtering off the yellow precipitate of [Pt$^{II}$(cis-dach)(N$_3$)$_2$] which was washed with water and ether. Crystals suitable for X-ray diffraction were grown in water at 4° C. $H_2O_2$ (25 mol equiv, 0.5 ml 30% $H_2O_2$, 4.9 mmol) was added to a suspension of [Pt$^{II}$(cis-dach)(N$_3$)$_2$] (0.067 g, 0.17 mmol) in water. The suspension was put in an ultrasonic bath for 10 min and then stirred overnight in the dark at ambient temperature.

EXAMPLE 7

Stability of Cis,trans,cis-[Pt$^{IV}$(N$_3$)$_2$(OH)$_2$(NH$_3$)$_2$]

The stability of the compound under various conditions was examined by comparing NMR spectra obtained at the beginning and end of the experimental periods.

a) The compound obtained from example 1 (2 mg) was dissolved in blood plasma (0.5 mls). No sign of any reduction product was detected after 2 weeks.

b) An aqueous solution of the compound obtained from Example 1 (5 mM) was prepared. No sign of any hydroysis was detected after 2 months.

c) A 5 mM solution of the compound obtained from example 1 was made up in 0.1M aqueous NaCl. The solution was examined after 2 days by means of NMR spectroscopy. No evidence of any azide ligand substitution in the compound from example 1 by chloride was found.

d) A 2 mM solution of the compound obtained from example 1 was made up in 5 mM aqueous glutathione. The solution was examined after having been kept in the dark for 8 weeks by means of NMR spectroscopy. No evidence of any reduction of the compound from example 1 by glutathione was found.

EXAMPLE 8

Photoactivation of Cis,trans,cis-[$Pt^{IV}(N_3)_2(OH)_2(NH_3)_2$] with Blue Light An aqueous solution of the compound obtained from example 1 as described in example 7b hereinabove, was irradiated with a low power energy light source at 20 mW with a wavelength of 457.9 nm, for 60 minutes. The solution was then examined by means of NMR spectroscopy which confirmed the presence of species containing the cis-[$Pt^{II}(NH_3)_2$] moiety.

In more detail irradiation was carried out using an argon-krypton ion laser (Coherent Innova 70C Spectrum) equipped with a fibre optic (FT-600-UMT, Ø (diameter) 600 µm; Elliot Scientific Ltd.) to deliver light ($\lambda$=457.9 nm, 488 nm, 647.1 nm) directly into the sample within the magnet of the NMR spectrometer. The laser output, after the fibre, was in the range of 10 to 75 mW, as measured by a Coherent 210 power meter. 1D $^1H$ and 2D [$^1H$, $^{15}N$] HSQC spectra were recorded on a Bruker DMX 500 NMR spectrometer ($^1H$ 500.13 MHz, $^{15}N$ 50.7 MHz) at a pH value of 5 using sodium 3-(trimethylsilyl)propionate-2,2,3,3-$d_4$ (TSP, 0 ppm) as internal $\delta(^1H)$ standard. When cis,trans-[$Pt^{IV}(en)(N_3)_2(OH)_2$] was analysed in a similar way 2D [$^1H$, $^{15}N$] HSQC-TOCSY spectra were also recorded. All $\delta(^{15}N)$ were referenced externally to $^{15}NH_4^+$ at $\delta$=0. pH values were measured with a pH-meter (Orion 710A) equipped with a microcombination electrode (Aldrich) calibrated with Aldrich standard buffers (pH 4, 7 and 10) and were adjusted with dilute solutions of $HClO_4$ and NaOH. No correction was made for $^2H$ isotope effects on the glass electrode.

EXAMPLE 9

Photoactivation of Cis,trans,cis-[$Pt^{IV}(N_3)_2(OH)_2(NH_3)_2$] with Blue Light and Binding to Dinucleotide The procedure of example 8 was repeated with a solution containing 1 mM GG dinucleotide [d(GpG)]. Examination of the solution after irradiation using NMR spectroscopy and electroscopy mass spectrometry showed binding of species containing the cis-[$Pt^{II}(NH_3)_2$] moiety to GG had taken place.

EXAMPLE 10

Photoactivation of cis,trans-[$Pt^{IV}(en)(N_3)_2(OH)_2$] with Red Light and Binding to Dinucleotide A low power energy light source (75 mW) with a wavelength of 647.1 nm was used to irradiate an aqueous 1 mM solution of the compound obtained from example 4 containing 1 mM GG dinucleotide [d(GpG)] for 18.5 hrs. The solution was examined by means of NMR spectroscopy which confirmed binding to the GG dinucleotide.

EXAMPLE 11

Binding to 14mer Polynucleotide

The procedure of example 9 was repeated with a 1 mM solution of a polynucleotide having the sequence ATACATGGTACATA, and using the compound obtained in example 2 in place of that obtained in example 1. Examination of the solution after photoactivation thereof, using NMR spectroscopy showed binding of species containing the cis-[$Pt^{II}(en)$] moiety to the GG moiety had taken place.

The invention claimed is:

1. A compound which is a Pt(IV) complex of the general formula I:

$$Pt(N_3)_2X^1X^2Y^1Y^2 \qquad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein said $R^1R^2NR^4NR^1R^2$ group is selected from bipyridyl, phenanthrolyl, 1,2-diaminophenyl and 1,2-diaminocyclohexyl.

2. A compound which is a Pt(IV) complex of the general formula I:

$$Pt(N_3)_2X^1X^2Y^1Y^2 \qquad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein $R^4$ represents an optionally substituted divalent, saturated or unsaturated, alkyl chain, said alkyl chain having 2 or 3 carbon atoms between the N atoms to which it is linked.

3. A compound according to claim 2 wherein one of $Y^1$ and $Y^2$ represents a further $N_3$ group.

4. A compound which is a Pt(IV) complex of the general formula I:

$$Pt(N_3)_2X^1X^2Y^1Y^2 \quad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$, and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein at least one of $Y^1$ and $Y^2$ represents an $OY^4$ group wherein $Y^4$ represents H or a $Y^5CO$ group wherein $Y^5$ represents R, RNH, or RCS, wherein R represents an optionally substituted C1 to C12 alkyl.

5. A compound which is a Pt(IV) complex of the general formula I:

$$Pt(N^3)_2X^1X^2Y^1Y^2 \quad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s), and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein $Y^3$ has the general formula $OOC(CY^6Y^7)_n CY^8Y^9O$ wherein each of $Y^6$ and $Y^7$ can represent H or a substituent or $Y^6$ and $Y^7$ together represent cycloalkyl and n is 0, 1 or 2 and each of $Y^8$ and $Y^9$ can represent H or a substituent or together represent oxygen.

6. A compound which is a Pt(IV) complex of the general formula I:

$$Pt(N_3)_2X^1X^2Y^1Y^2 \quad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein $Y^3$ is selected from oxalate or 1,1-dicarboxycyclobutane (CBDCA).

7. A compound which is a Pt(IV) complex of the general formula I:

$$Pt(N_3)_2X^1X^2Y^1Y^2 \quad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein said link between said at least two complexes comprises a C4 to C8 alkyl chain.

8. A compound which is a Pt(IV) complex of the general formula I:

$$Pt(N_3)_2X^1X^2Y^1Y^2 \qquad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein said compound is selected from:
Cis,trans,cis-[$Pt^{IV}(N_3)_2(OH)_2(NH_3)_2$],
Cis,trans-[$Pt^{IV}(en)(N_3)_2(OH)_2$] (where en represents ethylenediamine),
Trans,cis,cis-[$Pt^{IV}(OCOCH_3)_2(N_3)_2(NH_3)_2$],
[$Pt^{IV}(NH_3)_2(CBDCA)trans-(N_3)_2$] (where CBDCA represents 1,1-dicarboxycyclobutane), and
Cis,trans-[$Pt^{IV}(cis\text{-}dach)(N_3)_2(OH)_2$] (where dach represents diaminocyclohexane).

9. A process for generating a cytotoxic $Pt^{II}$ containing species comprising the steps of irradiating a compound with radiation effective for the reduction of said compound to liberate said $N_3$ groups wherein the compound is a Pt(IV) complex of the general formula I:

$$Pt(N_3)_2X^1X^2Y^1Y^2 \qquad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type.

10. A process for synthesizing a compound comprising the steps of bringing a compound of the formula $Pt^{II}(N_3)_2 X^1X^2$ into admixture with an oxidising agent under oxidising conditions and oxidising said $Pt^{II}(N_3)_2X^1X^2$ to a compound of the formula $Pt^{IV}(N_3)_2X^1X^2Q^1Q^2$ wherein $Q^1$ and $Q^2$ may be the same as $Y^1$ and $Y^2$ as defined hereinbefore or different, and, where $Q^1$ and/or $Q^2$ is a group(s) other than $Y^1$ or $Y^2$, respectively, or together represent a group other than $Y^3$, replacing any such $Q^1$, $Q^2$ or $Q^3$ group with said $Y^1$, $Y^2$ or $Y^3$ group(s), wherein the compound is a Pt(IV) complex of the general formula I:

$$Pt(N_3)_2X^1X^2Y^1Y^2 \qquad (I)$$

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s), and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type, wherein said oxidising agent is $H_2O_2$ and at least one of $Q^1$ and $Q^2$ is OH.

11. A process according to claim 10 wherein said oxidising agent is a halogen.

12. A method of treatment of a tumour in a patient comprising the steps of administering an effective dose of a compound to the patient, and subsequently irradiating the tumour with light having a wavelength effective for reducing said compound to a cytotoxic $Pt^{II}$ containing species, wherein the compound is a Pt(IV) complex of the general formula I:

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type.

13. A method of treating a cancer in a patient comprising the steps of administering an effective dose of a compound to the patient, and subsequently irradiating said compound with light having a wavelength effective for reducing said compound to a cytotoxic $Pt^{II}$ containing species, wherein the compound is a Pt(IV) complex of the general formula I:

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type.

14. A method of treatment of a condition in a patient in which abnormal cells are present in the body, comprising the steps of:

providing a compound wherein the compound is a Pt(IV) complex of the general formula I:

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type wherein one or more of $R^1$, $R^2$, $R^3$ and $R^4$ represents a covalently bonded link to a targeting moiety having affinity for said abnormal cell;

administering an effective dose of said compound to the patient; and irradiating the compound.

15. A pharmaceutical formulation comprising a compound or a pharmaceutically acceptable salt thereof in a pharmaceutically acceptable carrier therefor wherein the compound is a Pt(IV) complex of the general formula I:

wherein $X^1$ and $X^2$ are the same or different and each one represents a group of the general formula $NR^1R^2R^3$ wherein $R^1$, $R^2$ and $R^3$ are the same or different and in each case each one may represent any one of H and optionally substituted alkyl, aryl, aralkyl, acyl, cycloalkyl, heterocyclyl, alkenyl, aralkenyl, alkinyl, cycloalkenyl, or $X^1$ and $X^2$ together represent a group of the general formula $R^1R^2NR^4NR^1R^2$ wherein $R^1$ and $R^2$ have the same meaning as hereinbefore, and $R^4$ represents an optionally substituted divalent, saturated or unsaturated, alkyl chain, an optionally substituted divalent, saturated or unsaturated cycloalkyl or an optionally substituted divalent aryl, or $R^4$ or two or more of $R^1$, $R^2$, $R^3$ and $R^4$ and the respective N atom(s) to which they are linked, represent an optionally substituted heterocyclyl having at least one ring containing said N atom(s); and $Y^1$ and $Y^2$ are the same or different or, when in a cis position, as a further alternative they may together represent a divalent moiety $Y^3$, wherein at least one of $Y^1$ and $Y^2$, or $Y^3$, is a substantially labile ligand in the analogous Pt(II) complex corresponding to general formula (I) without the azide groups, whilst being substantially resistant, in vivo, to hydrolysis and physiological reducing agents, provided that one or more of $R^1$, $R^2$, $R^3$ and $R^4$, may further represent a covalently bonded link to at least one further complex of formula I so as to form a dimmer or oligomer, or to a targeting moiety having affinity for a predetermined tissue or cell type.

16. A pharmaceutical formulation according to claim 15 which is an oral formulation.

17. A pharmaceutical formulation according to claim 15 which is a parenteral formulation.

* * * * *

UNITED STATES PATENT AND TRADEMARK OFFICE
CERTIFICATE OF CORRECTION

PATENT NO. : 7,176,327 B2
APPLICATION NO. : 10/487758
DATED : February 13, 2007
INVENTOR(S) : Peter J. Sadler et al.

It is certified that error appears in the above-identified patent and that said Letters Patent is hereby corrected as shown below:

Column 6, line 9, replace, "$PtX^1X^1X^2$" with -- $PtX^1X^2$ --

Column 10, line 15, replace, "Trans, cis, cis-$Pt^{IV}$" with -- Trans, cis, cis – [$Pt^{IV}$ --

Column 12, line 23, replace, "cis – ($Pt^{II}$(en)]" with -- cis-[$Pt^{II}$(en)] --

Column 13, line 19, replace, "dimmer" with -- dimer --

Column 13, line 55, replace, "dimmer" with -- dimer --

Column 14, line 22, replace, "dimmer" with -- dimer --

Column 14, line 57, replace, "dimmer" with -- dimer --

Column 15, line 22, replace, "dimmer" with -- dimer --

Column 15, line 54, replace, "dimmer" with -- dimer --

Column 16, line 29, replace, "dimmer" with -- dimer --

Column 17, line 2, replace, "dimmer" with -- dimer --

Column 17, line 41, replace, "dimmer" with -- dimer --

Column 18, line 9, replace, "dimmer" with -- dimer --

Column 18, line 43, replace, "dimmer" with -- dimer --

UNITED STATES PATENT AND TRADEMARK OFFICE
CERTIFICATE OF CORRECTION

PATENT NO.         : 7,176,327 B2
APPLICATION NO. : 10/487758
DATED              : February 13, 2007
INVENTOR(S)       : Peter J. Sadler et al.

It is certified that error appears in the above-identified patent and that said Letters Patent is hereby corrected as shown below:

Column 20, line 3, replace, "dimmer" with -- dimer --

Signed and Sealed this

Twenty-eighth Day of August, 2007

JON W. DUDAS
*Director of the United States Patent and Trademark Office*